(12) United States Patent
Lader

(10) Patent No.: US 6,528,641 B2
(45) Date of Patent: *Mar. 4, 2003

(54) METHODS AND REAGENTS FOR PRESERVING RNA IN CELL AND TISSUE SAMPLES

(75) Inventor: Eric S. Lader, Austin, TX (US)

(73) Assignee: Ambion, Inc., Austin, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 09/771,256

(22) Filed: Jan. 26, 2001

(65) Prior Publication Data

US 2001/0016312 A1 Aug. 23, 2001

Related U.S. Application Data

(63) Continuation of application No. PCT/US99/17375, filed on Jul. 30, 1999, which is a continuation-in-part of application No. 09/127,435, filed on Jul. 31, 1998, now Pat. No. 6,204,375.

(51) Int. Cl.[7] ............... C07H 1/06; C07H 21/02; C07H 21/04; C12P 19/34; C12Q 1/68
(52) U.S. Cl. ............. 536/25.4; 536/25.41; 536/25.42; 435/6; 435/91.3
(58) Field of Search ............ 435/91.3, 6; 536/25.4, 536/25.41, 25.42

(56) References Cited

U.S. PATENT DOCUMENTS

| 4,746,539 A | * | 5/1988 | Webb et al. ............... 424/85 |
| 5,422,241 A | | 6/1995 | Goldrick et al. ............ 435/6 |
| 5,728,822 A | | 3/1998 | Macfarlane ............ 536/25.41 |
| 6,203,503 B1 | * | 3/2001 | Kelly et al. ............. 600/573 |
| 6,204,375 B1 | * | 3/2001 | Lader ..................... 536/25.4 |

FOREIGN PATENT DOCUMENTS

| EP | 0 707 061 | 4/1996 |
| EP | 0 772 972 | 5/1997 |

OTHER PUBLICATIONS

You et al., "*Cosedimentation of pea root polysomes with the cytoskeleton*", *Cell Biol. Int. Rep.* (1992), vol. 16 (7), pp. 663–673.*

Cathala et al., "A method for isolation of intact, translationally active ribonucleic acid," *DNA*, 2:329–335, 1983.

Chomczynski, "A reagent for the single–step simultaneous isolation of rna, dna and proteins from cell and tissue samples," *Biotechniques*, 15:532–536, 1993.

Chomczynski and Sacchi, "Single–step method of rna isolation by acid guanidinium thiocyanate–phenol–chloroform extraction," *Anal. Biochem.*, 162:156–159, 1987.

Foss et al., "Effects of fixative and fixation time on the extraction and polymerase chain reaction amplification and rna from paraffin–embedded tissue," *Diag. Mole. Path.*, 3:148–155, 1994.

Liedtke et al., "A comparison of methods for rna extraction from lymphocytes for rt–pcr," *PCR Methods and Applications*, 4:185–187, 1994.

* cited by examiner

Primary Examiner—W. Gary Jones
Assistant Examiner—Arun Chakrabarti
(74) Attorney, Agent, or Firm—Fulbright & Jaworski LLP

(57) ABSTRACT

This specification relates to the field of molecular biology and provides novel methods and reagents for preserving and protecting the ribonucleic acid (RNA) content of samples from degradation prior to RNA isolation. This preservation may be accomplished without ultra-low temperature storage or disruption of the tissue.

28 Claims, 9 Drawing Sheets

1   2   3   4

1 2 3 4 5     1 2 3 4 5     1 2 3 4 5

1 2 3 4 5    1 2 3 4 5    1 2 3 4 5

METHODS AND REAGENTS FOR PRESERVING RNA IN CELL AND TISSUE SAMPLES

The present application is a continuation of co-pending international application PCT US99/17375, filed Jul. 30, 1999, which is a continuation-in-part of co-pending U.S. patent application Ser. No. 09/127,435 filed Jul. 31, 1998 now U.S. Pat. No. 6,204,375. The entire text of each of the above-referenced disclosure is specifically incorporated by reference herein without disclaimer.

BACKGROUND OF THE INVENTION

1. Field of the Invention

The present invention relates to the field of molecular biology and provides a novel method and reagent for preserving and protecting the ribonucleic acid (RNA) content of tissue or cell samples from degradation prior to RNA isolation.

2. Description of Related Art

Obtaining high quality, intact RNA is the first and often the most critical step in performing many fundamental molecular biology experiments. Intact RNA is required for quantitative and qualitative analysis of RNA expression by Northern blot hybridization, nuclease protection assays, and RT-PCR.

There are many published reports which describe methods to isolate intact RNA from fresh (or quick frozen) cells or tissues. Most of these techniques utilize a rapid cell disruption step in which the tissue is dispersed in a powerful protein denaturation solution containing a chaotropic agent (e.g., guanidinium or lithium salt). This rapid disruption of cell membranes and inactivation of endogenous ribonuclease is critical to prevent the RNA from being degraded.

To obtain high quality RNA it is necessary to minimize the activity of RNase liberated during cell lysis and to prevent RNA degradation from other sources. This is normally accomplished by using isolation methods that disrupt tissues and inactivate or inhibit RNases simultaneously. For specimens low in endogenous ribonuclease, isolation protocols commonly use extraction buffers containing detergents to solubilize membranes, and inhibitors of RNase such as placental ribonuclease inhibitor or vanadylribonucleoside complexes. RNA isolation from more challenging samples, such as intact tissues or cells high in endogenous ribonuclease, requires a more aggressive approach. In these cases, the tissue or cells are quickly homogenized in a powerful protein denaturant (usually guanidinium isothiocyanate), to irreversibly inactivate nucleases and solubilize cell membranes. If a tissue sample can not be promptly homogenized, it must be rapidly frozen by immersion in liquid nitrogen, and stored at −80° C. Samples frozen in this manner must never be thawed prior to RNA isolation or the RNA will be rapidly degraded by RNase liberated during the cell lysis that occurs during freezing. The tissue must be immersed in a pool of liquid nitrogen and ground to a fine powder using mortar and pestle. Once powdered, the still-frozen tissue is homogenized in RNA extraction buffer. In the laboratory, quick freezing of samples in order to delay RNA extraction carries the penalty of a substantial increase in hands-on processing time. Processing multiple samples with liquid nitrogen and mortar and pestle is extremely laborious.

Quick freezing is even less convenient outside of the laboratory environment, but is still considered a necessity by those in the field. Scientists in the field collecting specimens for analysis do not have access to a high-speed homogenizer. They are forced to carry a supply of liquid nitrogen or dry ice large enough to store samples until they can be transferred to an ultra-low temperature freezer. Similarly, RNA extracted from human biopsy samples is usually partly or mostly degraded because pathologists do not routinely flash freeze specimens to preserve RNA.

There have been attempts to isolate RNA from archival samples that have not been prepared by the flash-freezing methodology. For example, Esser et al., 1995 claim the isolation of full length RNA from cells fixed with 5% acetic acid, 95% ethanol, with RNase inhibitors. However, in this paper, isolated cells in suspension were fixed in acetic acid/ethanol solution at −20° C. and then held at 4° C. for a relatively short time. Unfortunately, testing by the Inventor has shown that the Esser et al. 95% ethanol/5% acetic acid solution does not meet the performance standards required by the present invention. RNA recovered from both tissue samples and spleen cells in suspension kept at 4° C. for 20 hours appeared partially degraded, while RNA isolated from tissues stored at ambient temperature was completely degraded. Experiments reported in Esser et al. show that the method results in loss of RNA, due to leakage from the cells caused by ethanol. Using that method, 70% of the RNA is lost immediately upon fixation, and after 1 hour, 80% of the RNA is gone. Further, in a test where tissue samples and spleen cells were stored in the 95% ethanol/5% acetic acid solution at 25° C. overnight, the RNA of both the cell and tissue samples was completely degraded. Data is shown in FIG. 1.

The use of high purity, intact RNA is fundamental for performing various molecular biological assays and experiments such as Northern blot hybridization, nuclease protection assays, RT-PCR and medical diagnosis. The intrinsic instability of RNA and the presence of RNases in samples makes the isolation of intact RNA a difficult procedure. Further, the isolation and assay of RNA-containing samples is typically time consuming and tedious. The contamination of a molecular biology laboratory with RNases due to human error can have catastrophic results. Thus, there is an ongoing need to develop improved techniques, to make RNA isolation and assay methods more sensitive, more specific, faster, easier to use and less susceptible to human error and handling. It would therefore be advantageous in many instances, for research facilities to use automated RNA preservation protocol. For example, the present invention, could be combined with rapid RNA assay techniques or integrated nucleic acid diagnostic devices (U.S. Pat. No. 5,726,012, U.S. Pat. No. 5,922,591, incorporated by reference) for efficient, automated RNA preservation and analysis.

U.S. Pat. No. 5,256,571 reports a cell preservative solution comprising a water-miscible alcohol in an amount sufficient to fix mammalian cells, an anti-clumping agent and a buffering agent. At least one paper, Dimulescu et al., reports the apparent use of this fixative to preserve cervical cancer cells and cord blood lymphocytes prior to RNA isolation.

A large body of literature suggests that ethanol and acetone combinations are the best known fixatives for future recovery of nucleic acids from archival tissue. Yet, in view of the studies of the inventors, such ethanol/acetone mixture does not provide all of the desired characteristics of an RNA preservation medium. The mixtures do not protect RNA at ambient temperature, does not allow for the preservation of RNA in solid, multicell samples, and are also flammable, which makes it intrinsically less attractive as a general use reagent.

Some peripherally related art exists that deals with aspects of preserving or recovering RNA from fixed or preserved tissue samples. These reports include numerous evaluations of the suitability of histological fixatives to maximize the signal obtained by in situ hybridization to detect (not recover) RNA in tissue samples (for example U.S. Pat. Nos. 5,196,182 and 5,260,048). Other reports detail methods to recover fragmented RNA from fixed tissues for limited molecular analysis by PCR™ (Koopman et al., Foss et al., Stanta et al., Houze et al.). To recover this fragmented RNA, samples are typically treated with proteinase K to degrade the structural components of the tissue, then the RNA is extracted with a guanidinium-based solution. The RNA recovered from fixed tissue is of extremely poor quality, averaging in size of about 200 bases (Stanta 1991). This is probably due to a number of factors including the action of endogenous RNase and cross-linking of the RNA in the intracellular matrix during fixation. Since the RNA is mostly degraded, it can not be used for northern analysis or nuclease protection assays. It can be used in RT-PCR, but only for amplification of very small fragments.

The use of ammonium sulfate to precipitate proteins out of solution is known, but the use of ammonium sulfate to preserve RNA does not, to the Inventor's knowledge, appear in the art. Two reports describe the use of ammonium sulfate to investigate the folding and activity of mammalian ribonuclease A (Allewell et al. and Lin et al.). Allewell et al. investigated the effects of ammonium sulfate on the folding and activity of RNase A. At pH 5.5, the activity of ribonuclease A is suppressed to approximately 10% of the untreated control level across a broad range of ammonium sulfate concentration. This suppression of activity was expected by the authors. It appears to be due to a salt-induced denaturation of the protein. Unfortunately, even 10% RNase activity would substantially degrade the RNA of a sample over time. Therefore, this inhibition is not sufficient to protect RNA in many applications. When the ammonium sulfate is at pH 7.0, the activity of RNase A is suppressed at low concentrations as expected, but unexpectedly rises to 110% of the level of the untreated control at higher concentrations (3M). The authors theorize that the combination of the neutral pH and the high salt concentration forces a refolding of the protein into an alternate, highly active configuration. However, the Allewell et al. group were examining the activity of pure RNase A in solution, rather than in a cellular sample containing many RNases.

In view of the above, there is a need for methods and reagents that allow one to preserve and recover high quality, intact RNA from tissue samples stored at near ambient or ambient temperature.

SUMMARY OF THE INVENTION

The present invention relates to a novel method and reagents for preserving the RNA in tissue fragments at temperatures above the freezing point of the preservatives for extended periods of time, including days to months, prior to RNA isolation. There is no prior report disclosing any reagent or method similar to that described in this application. This breakthrough alleviates the necessity of either immediately processing samples to extract RNA, or the restriction of only isolating tissue at sites which have a supply of liquid nitrogen or dry ice.

The present application relates to compositions of RNA preservation media and methods of preserving RNA comprising: (1) obtaining an RNA-containing sample; and (2) treating the sample with an RNA preservation medium that infiltrates the sample, and protects the RNA from nucleases. In a preferred embodiment, the RNA preservation medium brings about the precipitation the RNA in the sample along with cellular protein in the sample. This co-precipitation of the RNA and cellular proteins is believed to render the RNA inaccessible to nucleases via physical means, while the action of the RNA preservation medium simultaneously inactivates or inhibits the action of the nucleases.

In some preferred embodiments, the RNA preservation medium comprises a salt that precipitates the RNA in the sample along with the cellular protein. In more presently preferred embodiments, the salt is a sulfate salt, for example, ammonium sulfate, ammonium bisulfate, cesium sulfate, cadmium sulfate, cesium iron (II) sulfate, chromium (III) sulfate, cobalt (II) sulfate, copper (II) sulfate, lithium sulfate, magnesium sulfate, manganese sulfate, potassium sulfate, sodium sulfate, or zinc sulfate. In presently preferred commercial embodiments, the salt is ammonium sulfate.

In RNA preservation media comprising salt, the salt is typically present in a concentration sufficient to precipitate the RNA in the sample along with the cellular protein. The salt is typically present in a concentration between 20 g/100 ml and the saturating concentration of the salt. Specifically, salt concentrations of 10, 15, 20, 25, 30, 35, 40, 45, 50, 55, 60, 65, 70, 75, 80, 85, 90, 95, 100, 110, 120, 130, 140, or 150 g/100 ml may be used, and the concentration may be a range defined between any two of these concentrations.

Of course, during use, some dilution of the salt concentration may occur due to, for example, liquid in the sample. Therefore, these salt concentrations may be higher than the final salt concentrations obtained in some uses. Further, it is contemplated that amounts of salt above the saturating concentration may be used in regard to the present invention. In such embodiments, there may be salt that is not in solution in the RNA preservation medium. This should not affect the RNA preservation abilities of the media. In fact, media having more than a saturating concentration of a salt may have some utility in applications where the media is added to a liquid sample. In such cases, upon addition to the liquid sample, salt which is not in solution prior to addition, may become soluble due to the increase in liquid volume. Thus, the final concentration of a salt can be at a level higher than that possible if a preservation medium containing a saturating or less than saturating salt concentration were used.

Preferred salts that have a solubility of greater than 20 g/100 ml are: ammonium sulfate, ammonium bisulfate, ammonium chloride, ammonium acetate, cesium sulfate, cadmium sulfate, cesium iron (II) sulfate, chromium (III) sulfate, cobalt (II) sulfate, copper (II) sulfate, lithium chloride, lithium acetate, lithium sulfate, magnesium sulfate, magnesium chloride, manganese sulfate, manganese chloride, potassium chloride, potassium sulfate, sodium chloride, sodium acetate, sodium sulfate, zinc chloride, zinc acetate, or zinc sulfate.

In a preferred embodiment, the salt is ammonium chloride at a concentration of between 20 g/100 ml and 100 g/100 ml, 30 g/100 ml and 100 g/100 ml, or 30 g/100 ml and 80 g/100 ml. In a currently preferred commercial embodiment, the salt is ammonium sulfate is in a concentration of 70 g/100 ml.

The present invention is not limited to the use of ammonium sulfate, and other salts or compounds will also be useful in protecting RNA in tissue samples and cell samples, for reasons as follows. The solubility of individual proteins depends greatly on the pH and salt concentration of the aqueous environment. Virtually all proteins are insoluble in pure water. As the ionic strength of the medium increases, proteins become more soluble. This is known as "salting in" of proteins. Above some ionic strength, the solubility of protein decreases. The precise conditions at which this occurs is unique for each protein/salt combination. In fact, at some salt concentrations, one protein may be completely insoluble while another is at its solubility maximum. This phenomenon is known as "salting out." Some salts have a much more dramatic salting out effect at high concentrations than others (e.g., $NO_3^- < Cl^- < acetate^- < SO_4^{2+}$). This phenomenon is the consequence of certain inherited characteristics of the ions (e.g., size, hydration, size, etc.). The present RNA protection media are believed to function due to the salting out effect of high levels of salt. The theory is that the salting out of proteins in the cells of the tissue samples or cell samples is what leads to the formation of RNA-protective protein/RNA complexes. The importance of the "salting out" phenomenon to this application is several-fold. First, it highlights that the effectiveness of RNA protection by protein precipitation using high concentrations of salt is complex and that certain combinations of ionic strength (salt concentration) and pH may make a particular salt much more effective in one formulation than at a different pH or concentration. Second, it provides a firm scientific foundation for the basic mechanism of action by the reagents in this application, and guides one in the search for additional RNA protective compounds within the scope of the invention. In order to determine whether another salt or putative RNA protective compound will function in the methods and reagents of the invention, one need merely obtain that salt or compound and test it in the manners described in the examples. By following the teachings of the examples, one of skill can easily elucidate whether a candidate substance is actually an RNA protective compound. Third, based on the theory that precipitation of intracellular proteins is the key to protecting RNA in situ, this explains why alcohol and acetone (agents that also can precipitate protein, albeit by a different mechanism) are partially active at protecting RNA in tissues, albeit not as protective as needed for most applications.

In some embodiments, the RNA preservation medium will comprise a combination of at least two salts that precipitate the RNA in the sample along with the cellular protein. In this manner, it might be that the total concentration of any given salt will not exceed 20 g/100 ml. However, in anticipated preferred embodiments, the combination of at least two salts is present in a total salt concentration sufficient to precipitate the RNA in the sample along with the cellular protein. In some embodiments, the total salt concentration is between 20 g/100 ml and 100 g/100 ml.

The RNA preservation medium may further comprise ethanol, methanol, acetone, trichloroacetic acid, 1-propanol, 2-propanol, polyethylene glycol, or acetic acid. These additional potential components can precipitate proteins in preserved cells and thereby protect RNA. However, these additional potential components are not salts. It is anticipated that in some embodiments, one will use these organic solvents in combination with a concentration of salt to obtain one of the inventive RNA preservation media described herein. For example, it is anticipated that a combination of one or more of these organic solvents in conjunction with less than 20 g /100 ml salt will accomplish the goals of the invention.

In some embodiments, the RNA preservation medium comprises a salt such as ammonium sulfate, ammonium bisulfate, ammonium chloride, ammonium acetate, cesium sulfate, cadmium sulfate, cesium iron (II) sulfate, chromium (III) sulfate, cobalt (II) sulfate, copper (II) sulfate, lithium chloride, lithium acetate, lithium sulfate, magnesium sulfate, magnesium chloride, manganese sulfate, manganese chloride, potassium chloride, potassium sulfate, sodium chloride, sodium acetate, sodium sulfate, zinc chloride, zinc acetate, zinc sulfate, methanol, trichloroacetic acid, 1-propanol, 2-propanol, polyethylene glycol, or acetic acid. Further, the RNA preservation medium may comprise a chelator of divalent cations, for example EDTA.

Typically, the RNA preservation medium comprises a buffer so that a constant pH can be maintained. For example, the buffer can be sodium citrate, sodium acetate, potassium citrate, or potassium acetate. In a presently preferred commercial embodiment, the buffer is sodium acetate. Typically, the RNA preservation medium has a pH of between 4 and 8. In presently preferred commercial embodiments, the pH is 5.2.

The sample preserved in the RNA preservation media may be any of a number of types of samples. For example, the sample may be a suspension of cells, such as bone marrow aspirates, white blood cells, sperm, blood, serum, plasma, bacteria, tissue culture cells, or algae. Alternatively, the sample may a solid tissue, for example, the tissue sample is from brain, heart, liver, spleen, thymus, kidney, testis, ovary, tumors, tissue biopsies, plant stems, roots, or leaves. In some cases, the sample may comprise an entire organism. For example, the organism may be a fish, insect, tadpole, coral, or embryo. In some protocols, it will be of benefit to hold an organism or sample in the RNA preservation medium during dissection. For example, it might be of benefit to dissect an organism in the RNA preservation medium when the sample comprises an organism that is a pathogen within a tissue sample or other organism. In this manner, the RNA of the pathogen may preserved. Further, the RNA of the tissue sample or other organism is preserved.

In many preferred methods, the practice of the invention will further comprise the step of isolating the preserved RNA. One of the advantages of the present RNA preservation media is that the RNA may be isolated from the tissue at a higher temperature than allowed with previous techniques. For example, the RNA may be isolated at a temperature that is greater than −20° C. In fact, the RNA may be isolated at room temperature.

In some cases, the sample may be stored in the RNA preservation medium prior to the isolation of the RNA. For example, the tissue is stored unfrozen at −20° C. to 45° C. Owing to the salt content of some of the RNA preservation media, samples are not frozen at −20° C. In preferred embodiments the sample may be stored at greater than 20° C.

The invention also contemplates kits for preserving RNA within a sample and isolating the RNA from the sample comprising: (1) an RNA preservation medium that infiltrates the sample and protects or partitions the RNA from nucleases; and (2) a reagent for performing an RNA extraction from the sample. In some embodiments, the reagent for performing an RNA extraction is a reagent for performing RNA extraction without organic solvents. Further, the reagent for performing an RNA extraction may be a reagent for performing a guanidinium-based RNA extraction. Alternatively, the reagent for performing an RNA extraction is a reagent for performing a lithium chloride-based RNA extraction.

In other embodiments of the present invention, a method of preserving RNA will comprise obtaining an RNA-containing sample, providing a salt and admixing the sample and the salt in a liquid to form an RNA preservation composition that infiltrates the sample and protects the RNA from nucleases. In one embodiment, the sample is comprised in the liquid prior to admixing the sample with the salt. In another embodiment, the salt is in a solid form prior to admixing with the sample and the liquid. In yet another embodiment, the salt is comprised in the liquid prior to admixing the sample with the salt.

In one embodiment of the invention, the sample is a blood cell and the liquid is blood serum. In another embodiment the sample is urine. In other embodiments, the liquid is water. In yet other embodiments, the liquid is a buffer.

In certain embodiments, RNA preservation compositions comprise obtaining an RNA-containing sample, providing a salt and admixing the sample and the salt in a liquid. The liquid can be a component of the sample, or added to the sample and salt. The salt is typically present in a concentration sufficient to precipitate the RNA in the sample along with the cellular protein. The salt is typically added so as to result in a final concentration in solution between 20 g/100 ml and the saturating concentration of the salt. In some cases, it will be efficient to add a very concentrated salt, a saturated salt or a supersaturated salt to a liquid sample. Adding salt that is likely to result in a greater than saturating concentration of salt in the final liquid sample has the advantages of quickly allowing RNA preserving concentrations to be reached and avoiding the need to carefully consider the amount of salt needed to reach a specific concentration in a given sample. Further, any salt that does not go into solution, will not affect the RNA preserving properties of the composition. Specifically, final salt concentrations of 10, 15, 20, 25, 30, 35, 40, 45, 50, 55, 60, 65, 70, 75, 80, 85, 90, 95, 100, 110, 120, 130, 140, or 150 g/100 ml may be used, and the concentration may be a range defined between any two of these concentrations. In some cases, a liquid containing more than a saturating concentration of salt may be employed, with the expectation that additional volume of liquid in the sample will result in dissolution of salt concentration.

In preferred embodiments, the salt is a sulfate salt, wherein the salt is ammonium sulfate. The ammonium sulfate is present in solution at a final concentration of between 20 g/100 mL and the saturating concentration of the salt. In preferred embodiments, the salt is present in solution at a final concentration of between 30 g/100 mL and 80 g/100 mL. In other embodiments, the RNA preservation composition comprises at least two salts, wherein the total salt concentration is present in solution at a final concentration of between 20 g/100 mL and 100 g/100 mL. In another embodiment, the RNA preservation composition comprises a chelator of divalent cations. In still other embodiments, the RNA preservation composition comprises a buffer, wherein said buffer has a pH between 4 and 8.

The solid components of the present invention (e.g., salts, buffers, and shelters), can be prepared to yield the desired final component concentrations in solution when added to an aqueous sample. The solid components can further be provided as powders, tablets, pills or other suitable formulations that provide the desired properties of an RNA preservation composition. Solid components can be directly added to a sample, added to a sample/liquid mixture, or present in a collection vessel prior to collection of a sample or sample/liquid mixture. The addition of excipients and bulking agents such as mannitol,. lactose, starch, cellulose, and the like, to provide desired solid charctersitics (i.e., improved solubility, storage stability, particle dispersion) are also considered in the formulation of powders, tablets and pills.

The solid components of the present invention can be added prior to sample collection, after sample collection or any combination thereof.

In one embodiment of the invention, pre-measured aliquots of a solid or liquid RNA preservation composition can be loaded into sample collection vessels, and an appropriate volume of a RNA-containing sample added. The collection vessel would then be agitated, dissolving any solid components of the RNA preservation composition, minimizing operator exposure to an RNA sample. For example, a solid RNA preservation composition could be any of the salts previously described. Thus, in particular embodiments of the invention, stabilizing RNA in a biological specimen such as blood or urine as described above is contemplated.

In one example, a vial for collecting specimen such as urine or blood could be supplied with pre-measured aliquots of a RNA preservation composition. Immediately following collection of said specimen, the vial could be agitated, admixing the RNA-containing specimen (i.e., sample) with the RNA preservation composition. A blood collecting vacuum vial comprising an outwardly projecting needle is contemplated for us in the present invention (U.S. Pat. No. 5,090,420, specifically incorporated herein by reference in its entirety) for rapid collection and mixing of RNA-containing samples. In one embodiment, automated RNA preservation is contemplated. Automated RNA preservation methods would be less tedious, faster, easier to use and less susceptible to human error and handling.

Also contemplated for use with pre-measured aliquots of a RNA preservation composition of the present invention are clinical specimen collection kits adapted for shipment by mail (U.S. Pat. No. 5,921,396, specifically incorporated herein by reference in its entirety). RNA-containing samples could be collected (e.g., away from a laboratory facility) and mixed with pre-measured aliquots of a RNA preservation composition provided in the vial, preserving RNA for shipment to a suitable RNA analysis site.

Alternatively, a RNA preservation composition can be pressed into a tablet or pill and stored in bulk. Tablets would be a convenient composition for storage and could be added in the correct quantity to a sample of any size in any container type. Thus, in other embodiments of the present invention, RNA preservation components in the form of tablets or pills are contemplated for field collection of samples from such sources as water reservoirs, sewage plants or the dairy industry. In certain instances, RNA preservation media comprising predetermined final salt concentrations or supersaturated salts could be supplied as packets. The RNA preservation salt or supersaturated salt packets would be especially useful in field studies, as there may be limited space or resources for analytical equipment. For example, packets could be supplied, as pre-measured and packaged as aliquots for a 1 mL, 5 mL, 10 mL, sample. Of course, any size packet, to accommodate a variety of salt quantities could be provided as either an anhydrous powder, hydrous powder, or a powder and liquid packaged individually or any combination thereof Thus, to preserve RNA in a sample, one would simply add the packet contents to a sample and mix.

Certain advantages of using a solid component RNA preservation composition would be weight savings in storage and transport, spills of solid components are less likely and reduced volume savings (i.e., preserving samples with dry reagents would minimize the final volume of the sample).

In other embodiments of the invention, RNA preservation compositions further comprise isolating the preserved RNA, wherein the RNA is isolated at a temperature that is greater than −20° C. In other embodiments, the sample is stored prior to the isolation of the RNA, wherein the sample is stored at temperatures greater than 0° C.

In particular embodiments, a composition of matter comprising an RNA-containing sample, a liquid, and a salt in a concentration sufficient to protect the RNA from nucleases. In preferred embodiments, the salt is a sulfate salt, wherein the sulfate salt is ammonium sulfate. In other embodiments, the composition comprises a combination of at least two salts. In another embodiment, the composition comprises a buffer, having a pH between 4 and 8. In yet another embodiment, the composition comprises a chelator of divalent cations.

The inventor's research indicates that 3M ammonium sulfate at pH 7.0 is quite effective at preserving intact RNA in intact tissue samples at all but extreme temperatures (37° C.–42° C.). It is proposed that upon application to the sample, the ammonium sulfate diffuses into the tissue and cells and causes cellular proteins to precipitate (probably along with RNA which is intimately associated with many different proteins in vivo) in protected complexes. In addition, RNase, which is localized in cytoplasmic vesicles, may also be precipitated and rendered inaccessible to cellular RNA.

It is believed that the mode of action of the claimed invention and the mode of action of the Allewell et al. mixture are different. If the mode of action of the inventive solutions were the same as seen by Allewell et al. one would expect the RNA isolated from tissues stored in the inventive buffers to be degraded. Allewell et al. reports that at pH 5 RNase is more active than normal. Thus, if RNAlater™ acted by the same mechanism, one would expect a boosting of the activity of RNase. Obviously, this would limit the ability of the RNA preservation media to preserve RNA. Based on the observation that such degradation does not occur, the present invention functions by a different mechanism than that described by Allewell et al.

The term "RNAlater™" is a trademark of Ambion, Inc., for certain commercial formulations of the RNA preservation media disclosed herein. In general, the term "RNAlater™" is employed to denote the formulation disclosed in Example 2, which is composed of 25 mM Sodium Citrate, 10 mM EDTA, 70 g ammonium sulfate/100 ml solution, pH 5.2. This reagent functions by rapidly infiltrating cells with a high concentration of ammonium sulfate, causing a mass precipitation of cellular proteins. Importantly, cellular structure remains intact. The advantage of this is that cells can be preserved and still identified histologically.

Following long-standing patent law, the words "a" and "an," when used in conjunction with the word "comprising" in the claims or specification, denotes one or more.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

Panel A at 4° C. (lanes 1–5:ethanol, acetic ethanol, acetone, acetic acetone, RNAlater™). Panel B shows identical lanes at 37° C. RNA isolated from mouse liver stored overnight at 4° C. (lanes 1–5) or 37° C. (lanes 6–10). Lanes 1 and 6, storage in ethanol. Lanes 2 and 7, storage in acidified ethanol pH 4.0. Lanes 3 and 8, storage in acetone. Lanes 4 and 9, storage in acidified acetone pH 4.0. Lanes 5 and 10, storage in RNAlater™.

Figure 1:
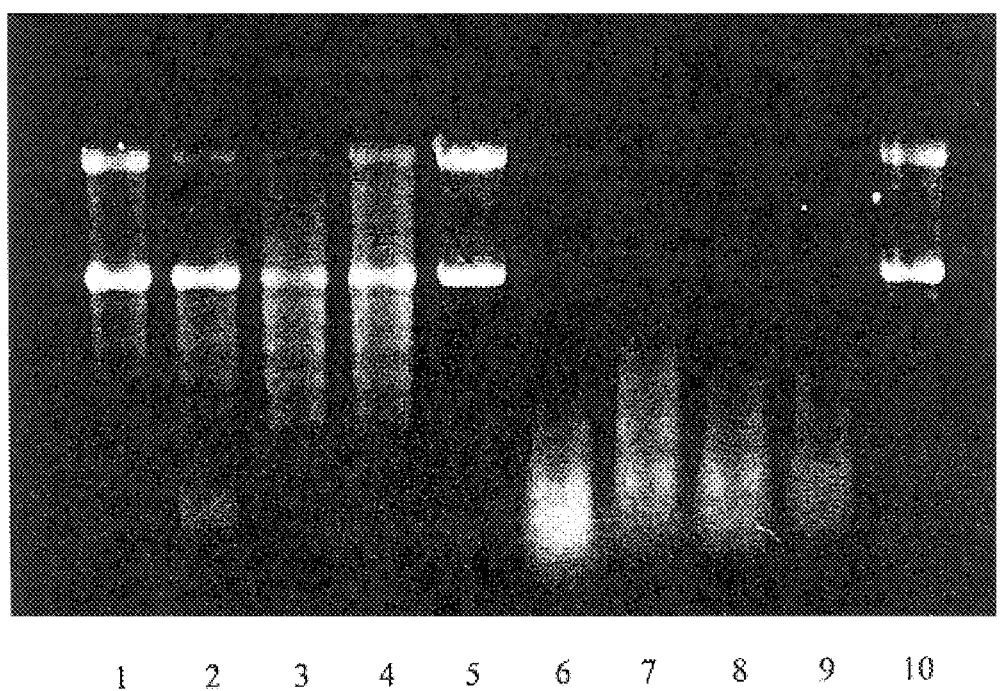
FIG. 1—Alcohol and Acetone are Unsuitable for Preserving Cellular Samples.
Figure 2:
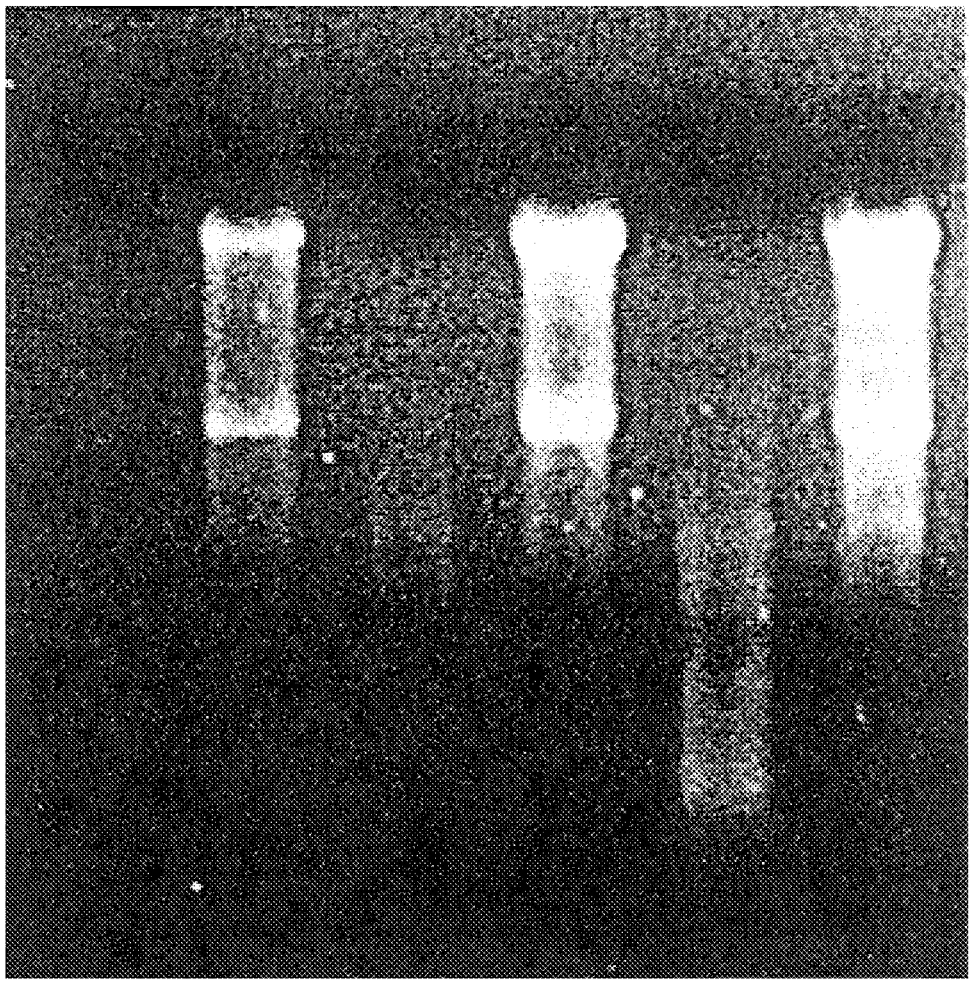

FIG. 2—RNA in Fresh Tissue Samples is Labile.

Fresh mouse liver (lanes 1 and 2), testis (lanes 3 and 4), and spleen (lanes 5 and 6) samples were placed either in RNAlater™ (lanes 2,4, and 6) (25 mM Sodium Citrate, 10 mM EDTA, 70 gm Ammonium Sulfate/100 ml solution, pH 5.0) or in a 4 molar guanidinium isothiocyanate (GITC) based RNA extraction solution (lanes 1, 3, and 5) at 4° C. for 12 hours. RNA was extracted and analyzed by gel electrophoresis. Intact RNA is observed only in lanes corresponding to tissues preserved in RNAlater™ (lanes 2, 4, and 6).

Figure 3:
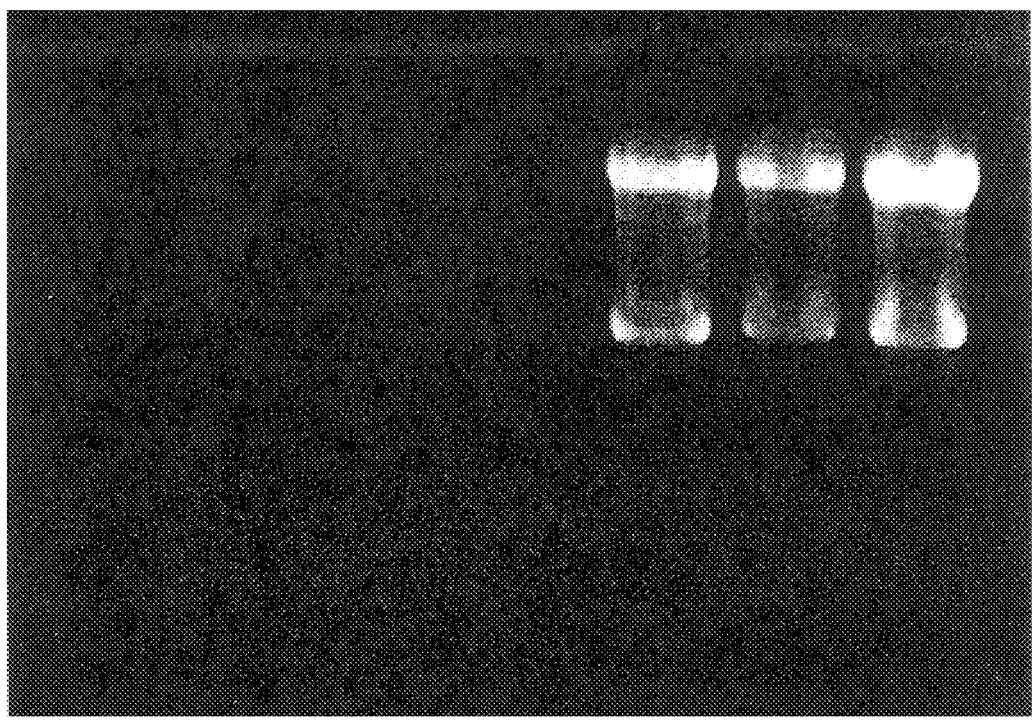

FIG. 3—Defining the Effective Concentration Range of Ammonium Sulfate that protects RNA in Tissue.

Fragments of freshly isolated mouse liver was placed in RNAlater™ with various amounts of Ammonium Sulfate. Samples contained 0, 10%, 20%, 30%, 40%, 50%, or 70% Ammonium Sulfate (lanes 1–7 respectively). After incubation at 4° C. for 24 hours, RNA was extracted from the sample and analyzed by denaturing agarose gel electrophoresis.

Figure 4:
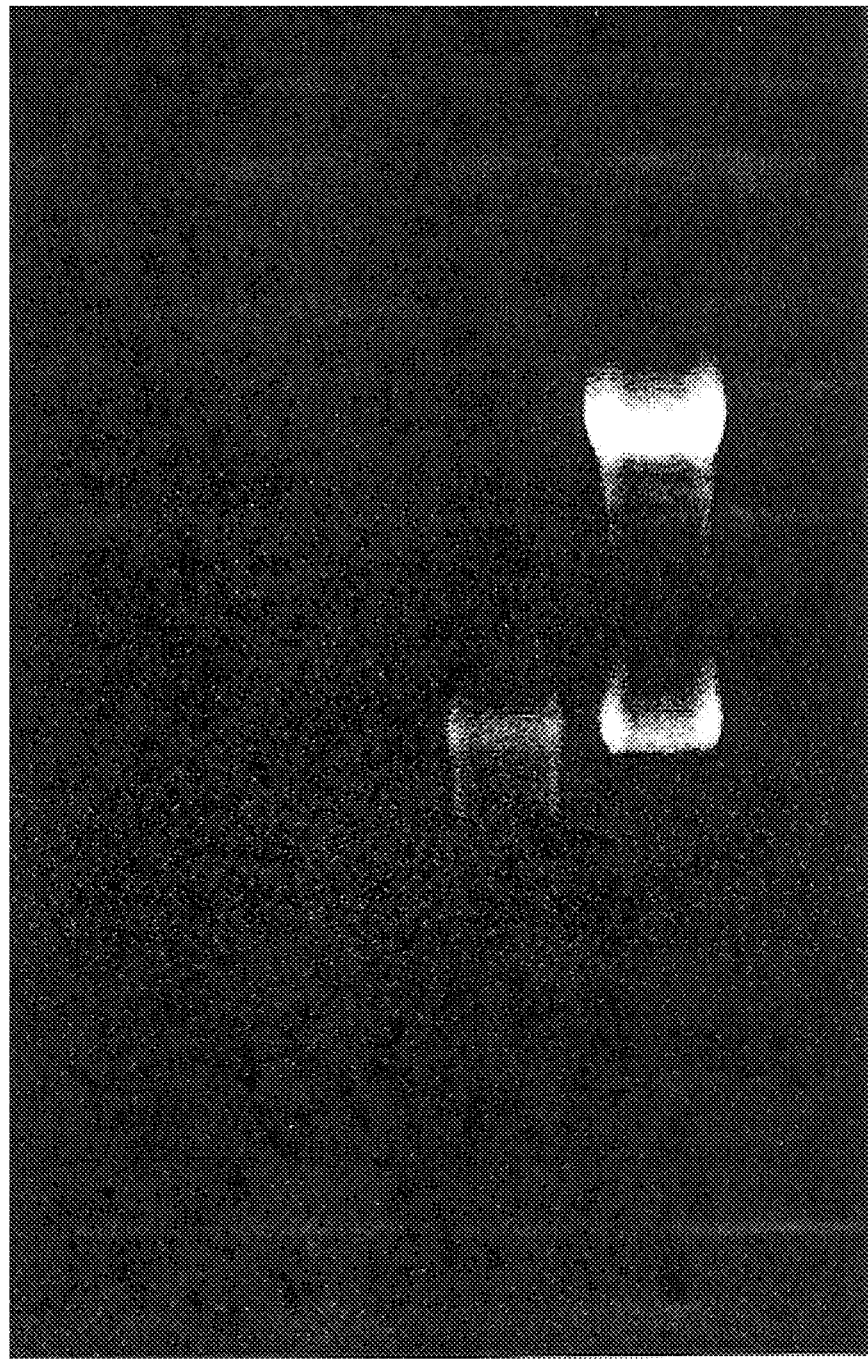

FIG. 4—Enhancing the Potency of RNAlater™ at Extreme Temperatures by Optimizing both pH and Ammonium Sulfate Concentrations.

The effects of pH and Ammonium Sulfate at extreme temperatures was assessed. Fresh mouse liver was stored at room temperature or 37° C. for 24 hours in 4 formulations of RNAlater™ solution. Lane 1: pH 7.0, 70 g/100 ml Ammonium Sulfate, Lane 2: pH 5.0, 55 g/100 ml Ammonium Sulfate, Lane 3: The original RNAlater™ formulation (which contained 55 g/100 ml Ammonium Sulfate at pH 7.0), Lane 4:pH 5.0 and 7g/100 ml Ammonium Sulfate concentration.

Figure 5A:
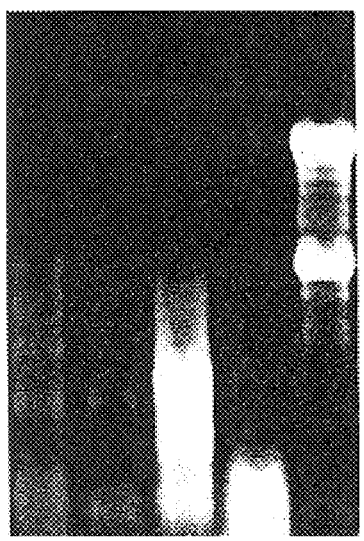
Figure 5B:
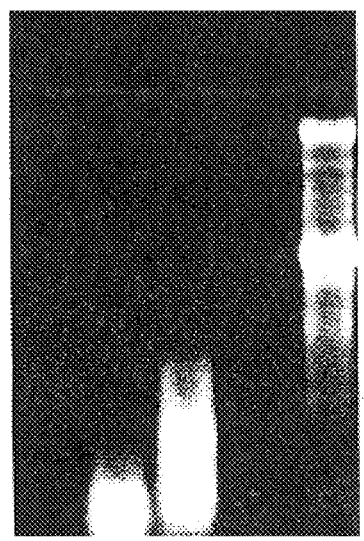
Figure 5C:
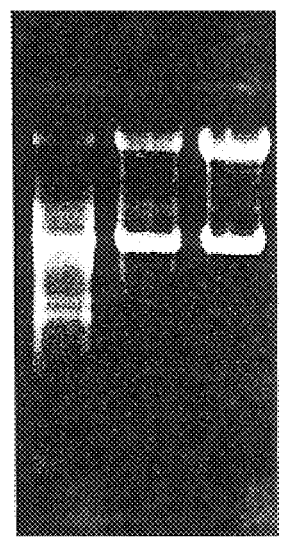

FIG. 5—The Specificity of Ammonium Sulfate on the Effectiveness of RNAlater™.

Panel A and B: Fresh liver samples were incubated in 5 buffers for 3 days at 25° C. (panel A) and 37° C. (panel B), lane 1; RNAlater™ with ammonium carbonate, lane 2; with ammonium chloride, lane 3; with potassium sulfate, lane 4; with magnesium sulfate lane 5; Ammonium Sulfate. Panel C: Fresh liver incubated overnight at 4° C. in RNAlater™ containing: lane 1, Cesium Chloride; lane 2, Cesium Sulfate; lane 3, Ammonium Sulfate.

Figures 6A, 6B, 6C:
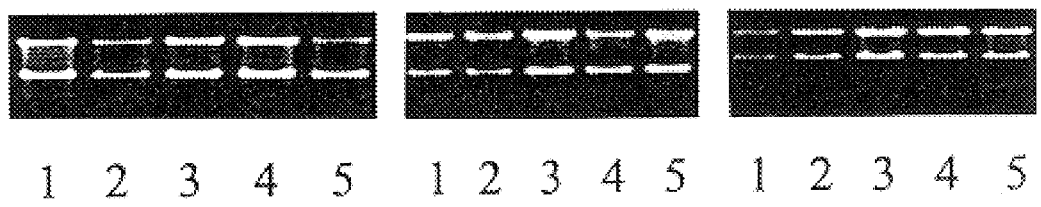

FIG. 6—RNA Isolated from Mammalian Tissues Stored at 4° C. in RNAlater™.

Fresh mouse brain, heart, kidney, liver, and spleen (lanes 1–5) were placed in RNAlater™ solution and stored at 4° C. After incubation of one week (panel A), 2 weeks (panel B), and 4 weeks (panel C), RNA was extracted from the tissue samples and analyzed by denaturing agarose gel electrophoresis.

Figures 7A, 7B, 7C:

FIG. 7—RNA Isolated from Mammalian Tissues Stored at Ambient Temperature (25° C.) in RNAlater™.

Fresh mouse brain, heart, kidney, liver, and spleen (lanes 1–5) were placed in RNAlater™ solution and stored at 25° C. (ambient temperature). After incubation of two weeks (panel A) or 4 weeks (Panel B), RNA was extracted from the tissue samples and analyzed by denaturing agarose gel electrophoresis.

Figure 8:
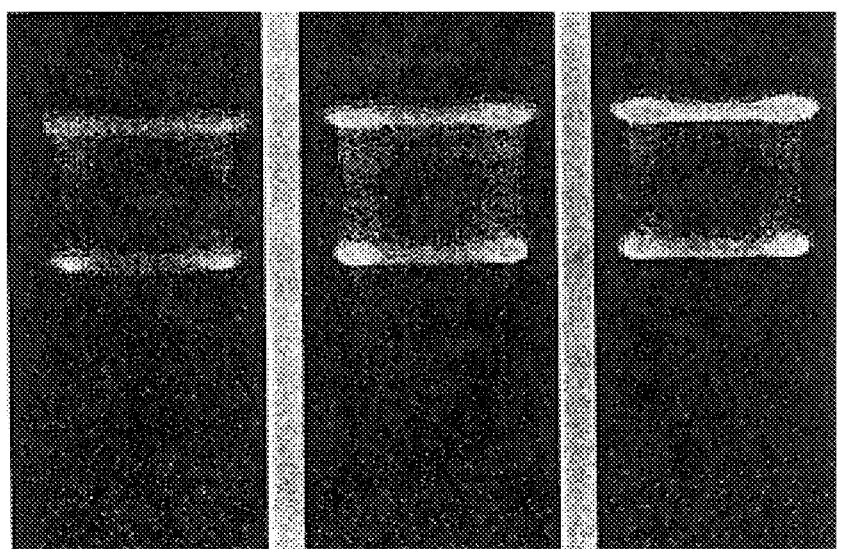

FIG. 8—RNA Isolated from Mammalian Tissue Stored at Extreme Temperatures (37° C.) in RNAlater™.

Fresh mouse liver, kidney, and spleen (lanes 1–3) were placed in RNAlater™ solution and stored at 37° C. After incubation for three days, RNA was extracted from the tissue samples and analyzed by denaturing agarose gel electrophoresis FIG. 9—Using the Ambion to make RNA from Tissues Preserved in RNAlater™.

Lanes 1–3 are liver, heart, and kidney, ToTally RNA™, lanes 4–6 are RNAqueous™. Fresh mouse liver (lanes 1 and 4), heart (lanes 2 and 5), and kidney (lanes 3 and 6) samples were placed in RNAlater™ and stored overnight at 4° C. RNA was isolated from size matched samples using either the Ambion ToTally RNA™ kit (lanes 1–3) or the Ambion RNAqueous™ kit (lanes 4–6). Lane 1—molecular weight marker.

DESCRIPTION OF ILLUSTRATIVE EMBODIMENTS

The present invention relates to the field of molecular biology and provides novel methods and reagents for preserving and protecting the ribonucleic acid (RNA) content of RNA-containing samples from degradation prior to RNA isolation. Strikingly, this is accomplished without ultra-low temperature storage or disruption of the samples. For example, isolated human biopsy tissue can be placed in a RNA preservation medium and stored refrigerated for an extended period of time, until the researcher has time to extract RNA for analysis.

The following examples illustrate the utility of the present invention. All examples make use of fresh animal or plant tissues, living cells in suspension or other samples containing RNA. The methods and compositions are applicable for the preservation of RNA from a broad range of bacterial, plant, and animal species, including humans. RNA samples recovered in these experiments were analyzed by formaldehyde/agarose gel electrophoresis, staining with ethidium bromide, and illumination with 300 nm ultraviolet light, as described in Molecular Cloning, A Laboratory Manual. (Maniatis, et al.).

The examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Criteria for Analysis of RNA to Determine if it is "Intact"

The Inventor routinely performs assays on RNA designed to assess the intactness of such samples. This criterion was used in the examples that follow to objectively gauge the quality of the RNA recovered from tissues preserved in RNAlater™, other inventive RNA preservation media, or other solutions.

RNA is analyzed by electrophoresis on formaldehyde agarose gel using the basic protocol described in "Molecular Cloning, a Laboratory Manual" (Maniatis, Fritsch, Sambrook, eds., Cold Spring Harbor Press). In order to visualize the RNA in the gel, the intercalating dye Ethidium Bromide is added to the samples. Ethidium Bromide, when intercalated into nucleic acid, fluoresces under ultraviolet light, permitting visualization of the nucleic acid. Intact RNA appears as a broad smear of heterogeneous mRNA (from 0.5 kilobase up to ~10 kilobase), with two very prominent, discrete bands, (28S and 18S ribosomal RNA), superimposed on the background smear in a 2:1 ratio. There should be very little evidence of discrete bands intermediate in size between 18S and 28S RNA. Partially degraded RNA is characterized by a loss of high molecular heterogeneous RNA, multiple smaller ribosomal RNA cleavage products, and a deviation from the 2:1 ratio of 28S to 18S (28S is more sensitive to degradation). Severely degraded RNA will have 28S:18S ratios less than 1:1, and exhibit a smear of degraded ribosomal RNA from ~2 kilobase down to <0.1 kilobase.

"Partially degraded," as used in this specification means that the ratio of 28S:18S rRNA is aberrant and may be as low as 1:1, but the rRNA bands are still distinct.

"Mostly degraded," as used in this specification means that the ratio of 28S:18S is below 1:1. 28S may be barely visible, but there is still nucleic acid in a smear extending from the approximate position of 28S rRNA down.

"Completely degraded," and "degraded," as used in this specification means that the only RNA present is in a low molecular weight smear below the normal position of 18S rRNA

EXAMPLE 2

Preparation of an Exemplary RNAlater™ RNA Preservation Medium

The description in this example provides one manner in which RNAlater™ can be prepared. First, one should prepare or obtain the following stock solutions and reagents: 0.5 M EDTA disodium, dihydrate(18.61 g/100 ml, pH to 8.0 with NaOH while stirring); 1M Sodium Citrate trisodium salt, dihydrate (29.4 g/100 ml, stir to dissolve); Ammonium Sulfate, powdered; Sterile water.

In a beaker, combine 40 ml 0.5 M EDTA, 25 ml 1M Sodium Citrate, 700 gm Ammonium Sulfate and 935 ml of sterile distilled water, stir on a hot plate stirrer on low heat until the Ammonium Sulfate is completely dissolved. Allow to cool, adjust the pH of the solution to pH5.2 using 1M $H_2SO_4$. Transfer to a screw top bottle and store either at room temperature or refrigerated.

EXAMPLE 3

Exemplary General Manner of Preserving Tissue in RNA Preservation Media

Tissue samples to be stored in RNAlater™ or other inventive RNA preservation media should be excised from the source as quickly as possible and placed in RNAlater™ or other inventive RNA preservation media. Some tissue samples may have a protective membrane or other barrier that would impede the rapid infusion of RNAlater™ or other inventive RNA preservation media, such as a waxy coating on a leaf or the capsule of a kidney or testis. These protective barriers should be disrupted to allow rapid infiltration of the RNAlater™ or other inventive RNA preservation media into the sample. In addition, large samples should be dissected into smaller fragments to maximize diffusion. As a general guideline, sample thickness would be limited to 0.5 cM in at least two dimensions. Samples that consist of cells in suspension should be concentrated into a small volume by gentle centrifugation at a g-force sufficient to pellet the cells without damage, resuspended in a minimal volume of the removed supernatant, then mixed with 5 volumes of RNAlater™ or other inventive RNA preservation media (v/v). If concentration is not possible, the cell suspension should be diluted in 10 volumes of RNAlater™ or other inventive RNA preservation media. Alternatively, any other volume of liquid, essential media or amount of a solid RNA preservation composition which results in the preservation of RNA scan be used. Since the buffer will not disrupt the cells, concentration by centrifugation can be performed later.

Samples that are to be stored for 1 week or less may be stored at ambient temperature (25° C.). For extended stability, samples should be stored refrigerated. For permanent archival storage (months–years), samples may be stored in a standard freezer (−20° C.). To isolate RNA from treated samples, tissue samples should be transferred directly into tissue extraction buffer. Cells in suspension must be pelleted by centrifugation , the n resuspended in RNA extraction buffer and processed.

EXAMPLE 4

RNA in Fresh Tissue Samples is Labile

Fresh mouse liver, testis, and spleen samples (∼0.5 cm$^3$) were placed either in RNAlater™ or in a 4 molar guanidinium isothiocyanate (GITC) based RNA extraction solution, or water at 4° C. for 12 hours. This guanidinium solution is a typical RNA extraction buffer (and found in Ambion's commercially available ToTally RNA™ and RNAqueous™ kits). GITC is a powerful chaotropic agent used either alone or in conjunction with other reagents in virtually all RNA isolation protocols. After an overnight incubation, RNA was extracted from the tissue samples and analyzed by denaturing agarose gel electrophoresis. Intact RNA was observed only in lanes corresponding to tissues preserved in RNAlater™. RNA extracted from samples stored in GITC was badly degraded. Thus, GITC does not preserve the RNA in intact tissue samples. Animal tissues stored in water or biological buffers such as normal saline yield no measurable RNA after an identical overnight incubation. Data is shown in FIG. 2.

EXAMPLE 5

Determining the Effective Concentration of Ammonium Sulfate that Protects RNA in Tissue Freshly isolated mouse liver was placed in a variety of putative RNA preservation media with various concentrations of ammonium sulfate. Samples contained 0, 10%, 20%, 30%, 40%, 50%, or 70% Ammonium Sulfate. After incubation at 4° C. for 24 hours, RNA was extracted from the sample and analyzed by denaturing agarose gel electrophoresis.

In the sample with no ammonium sulfate, all that is observed is a low molecular weight smear. No specific banding of ribosomal RNA can be observed. At 10% ammonium sulfate, slight evidence of rRNA bands can be observed. At 20% ammonium sulfate, the 18S band is more obvious, and there is more of a smear of degraded 28S rRNA extending down from the anticipated position of 28S rRNA. No specific 28S band is observed. At 30% ammonium sulfate, both 28S and 18S rRNA bands are visible, however there is extensive degradation (based on the aberrant ratio of 28S:18S, and numerous smaller bands observed. The sample with 40% ammonium sulfate appears mostly intact, and the yield is 10 fold higher than at 30%. While these experiments suggest a minimum requirement for 30–40% ammonium sulfate for protection of tissue RNA, the effective concentration will depend on the type of tissue, the size of the tissue fragment, the storage temperature, and the period of storage.

Under more stringent incubation conditions, a higher concentration of ammonium sulfate is necessary for preservation of the RNA. For example, 55 g /100 ml is required for protection of RNA in tissue samples at 25° C. and, as described in Example 6 70 g/100 ml appears required for maximal protection of RNA in tissue samples at 37° C. Further, if samples are stored in 55 g or less ammonium sulfate at 37 degrees for 24 hours, at least some studies yield partially degraded RNA as judged by a 1:1 ratio of 28S:18S rRNA. Data is shown in FIG. 3.

EXAMPLE 6

Enhancing the Potency of RNA Preservation Media at Extreme Temperatures by Optimizing both pH and Ammonium Sulfate Concentrations The effect of pH and ammonium sulfate at extreme temperatures was assessed. Fresh mouse liver was placed in 4 formulations of test RNA preservation media solution and stored at room temperature, or 37° C., for 24 hours. RNA was extracted from the tissue samples and analyzed by denaturing agarose gel electrophoresis. The formulation which contained 55 g/100 ml ammonium sulfate at pH 7.0 was effective at ambient temperature, but did not fully protect the RNA at 37° C. A combination of low pH (5.0) and a higher ammonium sulfate concentration (70 g/100 ml) was much more effective at high temperatures than the original formulation and yielded intact RNA after 3 days at 37° C. Neither modification alone (low pH or higher ammonium sulfate concentration) appreciably enhanced the stability of the RNA above that provided by the original formulation. Data is shown in FIG. 4.

EXAMPLE 7

The Specificity of Ammonium Sulfate on the Effectiveness of RNA Preservation Media Four additional formulations of test RNA preservation media were produced. The ammonium sulfate was replaced with saturating amounts of ammonium carbonate, ammonium chloride, potassium sulfate, or magnesium sulfate. Fresh liver samples were incubated in these buffers for 3 days at 25° C. and 37° C. RNA was extracted and analyzed by denaturing agarose gel electrophoresis. Only the ammonium sulfate control prevented the RNA from being degraded. Maximum protection appears to require high concentrations of both ammonium and sulfate ions. Ammonium sulfate is probably the most effective of the salts tested because it is far more soluble in water than these other salts, enabling formulations with very high salt content. This hypothesis was challenged by evaluating two esoteric (and more expensive) salts; cesium sulfate (which is quite soluble—saturation at 362 g/100 ml) and cesium chloride (70 g/100 ml). These salts were substituted (in equal mass) for the ammonium sulfate in the solution described in Example 2 and processed liver samples as above. Cesium sulfate and cesium chloride offered partial protection to the liver RNA at 4° C. Taken together, the data suggest that of the salts tested, ammonium sulfate has superior ability to protect RNA from degradation in intact tissues. However, the partial protection the inventors see with high concentrations of other salt suggests a shared mechanism of action, with varying degrees of efficacy. Data is shown in FIG. 5.

EXAMPLE 8

RNA Isolated from Mammalian Tissues Stored at 4° C. in RNAlater™

Fresh mouse brain, heart, kidney, liver, and spleen samples were placed in RNAlater™ solution, prepared as taught in Example 2, and stored at 4° C. After incubation of one week, 2 weeks, and 4 weeks, RNA was extracted from the tissue samples and analyzed by denaturing agarose gel electrophoresis. All the RNA samples were intact. Fresh mouse brain, kidney, liver, and spleen samples were placed in 10 volumes of RNAlater™ and stored at 4° C. After one week, two week, and four week incubations, equivalent weight fragments of tissue were removed and processed. Each tissue sample was placed in a guanidinium isothiocyanate lysis solution, homogenized, and isolated using the Ambion RNAqueous™ kit (as described in Example 20). The concentration of the RNA was determined by measuring the absorbence at $O.D._{26}$. The RNA was analyzed by formaldehyde-agarose gel electrophoresis as described in Example 1.

All RNA samples were judged "intact" based on clean, sharp ribosomal RNA bands in a 2:1 ratio of 28S:18S. In addition, overall quality was judged by a visible background smear of heterogeneous RNA and a lack of visible breakdown products from ribosomal RNA. Data is shown in FIG. 6.

EXAMPLE 9

RNA Isolated from Mammalian Tissues Stored at Ambient Temperature (25° C.) in RNAlater™

Fresh mouse brain, heart, kidney, liver, and spleen samples were placed in RNAlater™ solution and stored at 25° C. (ambient temperature). After incubation for two or four weeks, RNA was extracted from the tissue samples and analyzed by denaturing agarose gel electrophoresis as described above. The RNA recovered after two weeks was intact. RNA recovered after a one month incubation was still ~50% intact as judged by the appearance of the 18S and 28S ribosomal RNA bands. Data is shown in FIG. 7.

EXAMPLE 10

RNA Isolated from Mammalian Tissue Stored at Extreme Temperatures (3° C.) in RNAlater™

Fresh mouse liver, kidney , and spleen samples were placed in RNAlater™ solution and stored at 37° C. After incubation for three days, RNA was extracted from the tissue samples and analyzed by denaturing agarose gel electrophoresis, as described above. The RNA isolated was intact. The RNA isolated from tissues incubated one week— 10 days is partially degraded (~50% intact). This RNA is still a suitable substrate for Nuclease Protection Assays or RT-PCR (Reverse Transcriptase-Polymerase Chain Reaction) both of which procedures are known to those of skill in the art. Data is shown in FIG. 8.

EXAMPLE 11

RNA Isolated from Amphibian, Fish, Insect, Bacteria, and Plant Tissue Stored at 4° C. in RNAlater™

The Inventor tested the effectiveness of RNAlater™ to preserve the RNA in Xenopus heart and liver, goldfish liver, whole beetle, whole Drosophila, *E. Coli*, tobacco, and alfalfa. Each were placed in RNAlater™ solution and stored at 4° C. After incubation for 24 hours, RNA was extracted from the samples and analyzed by denaturing agarose gel electrophoresis as described in Example 1. All RNAs appeared intact. This demonstrates the effectiveness of RNAlater™ as a general reagent useful for tissues from diverse organisms.

EXAMPLE 12

Demonstration of the Suitability of RNAlater™ RNA as Target in Northern Hybridization Analysis Fresh mouse liver, kidney, and spleen samples, were incubated in RNAlater™, for 24 hours at 25° C. or 37° C. RNA was extracted, resolved by denaturing agarose gel electrophoresis, transferred to a positively charged nylon membrane (Brightstar Plus™, Ambion, Austin, Tex.), and hybridized with a radiolabeled antisense β Actin RNA probe according to manufacturers recommendations (Northern Max™ Kit, Ambion, Austin, Tex.). The discrete signal corresponding to the 1.8 kilobase β Actin transcript detected in all samples indicate that the messenger RNA in all samples was completely intact and available for hybridization by northern analysis.

EXAMPLE 13

The Suitability of RNAlater™ RNA as Template for RT-PCR Analysis

RNA prepared from mouse liver, spleen, kidney, and testis stored in RNAlater™ for 24 hours at 37° C. was used as template for RT-PCR with two pairs of PCR™ primers for constituitively expressed genes (the housekeeping genes cyclophilin and RIG/S15) in a multiplex RT-PCR amplification. The expected products (216 bp cyclophilin, 324 bp RIG/S15) were obtained in all cases. Thus, the recovered RNA is suitable for RT-PCR analysis.

EXAMPLE 14

Use of RNA Preservation Media to Protect Clinical Samples

There is an increasing trend towards genetic analysis of human clinical samples by RT-PCR. These clinical samples include solid tumors, isolated cells, serum, urine, blood, or feces. Biopsies of solid tumors are frequently analyzed for the expression of specific indicator genes like p53, whose aberrant expression plays a pivotal role in a number of cancers. White blood cells isolated from normal or leukemic blood are frequently analyzed for expression of interleukin genes. Urine, blood, serum, plasma, and feces are frequently analyzed for the presence of pathogenic organisms. In an anticipated use, RNAlater™ or other inventive RNA preservation media can be used as a holding buffer for patient specimens isolated in a clinical setting. The RNA in these samples would then be protected until the samples could be transferred to a laboratory setting where intact RNA would be extracted for analysis. In an anticipated use, RNAlater™ or other inventive RNA preservation media can be used to stabilize normally unstable viral RNA (such as HIV) in blood products for subsequent diagnosis.

EXAMPLE 15

Use of RNA Preservation Media to Preserve Field Specimens

Field biologists throughout the world face the common problem of how to preserve samples collected in the field for later analysis in the laboratory. Often research into RNA expression is simply avoided due to the logistical difficulties involved in maintaining specimens frozen in dry ice or liquid nitrogen. In an anticipated use, RNAlater™ or other inventive RNA preservation media may be used as a holding buffer for specimens isolated in the field by scientists who need to preserve samples until a later return to the laboratory environment. An important benefit of RNAlater™ or other inventive RNA preservation media is that small specimens (such as microorganisms) remain intact. Thus, complex specimens such as a population of microorganisms isolated from water samples can be preserved en masse, sorted by classification in the laboratory, then analyzed for gene expression.

EXAMPLE 16

Use of RNA Preservation Media as a Dissection Medium

Biologists must frequently perform a complicated dissection in order to isolate a specimen for RNA analysis. Often the time delay means that RNA isolated from the sample will be of poor quality. Developmental biologists studying early mouse embryonic development must perform meticulous dissections to isolate early embryos from the decidua of the uterus. In another example, neuroanatomists must perform complicated dissections to remove a specific part of a brain for RNA analysis. In an anticipated use, RNAlater™ or other inventive RNA preservation media would be a very effective dissection medium. Immersing a sample in RNAlater™ or other inventive RNA preservation media will protect the RNA during dissection, while preserving sample integrity (other reagents, such as guanidinium would cause extensive cellular lysis and compromise the dissection). Using RNAlater™ or other inventive RNA preservation media would facilitate a lengthy dissection of a sample without the fear that RNA in the sample will be degraded.

EXAMPLE 17

Use of RNA Preservation Media to Preserve Samples for Pathogenic Testing

Nucleic acid analysis to detect and classify pathogenic organisms is a fast growing technology. In an anticipated use, RNAlater™ or other inventive RNA preservation media may be used as a holding buffer for specimens collected by health inspectors in the field. Placing samples in RNAlater™ or other inventive RNA preservation media would preserve the RNA in the samples. The samples could then be analyzed using nucleic acid technology for the presence of pathogenic organisms. For example, a USDA inspector could collect samples of meat from a slaughterhouse and place them in RNAlater™ or other inventive RNA preservation media. The RNA in pathogenic organisms present on the surface of the sample would be preserved intact. The meat can later be removed from the sample, the pathogens recovered from the RNAlater™ or other inventive RNA preservation media, and the RNA isolated for analysis. One important feature of RNAlater™ or other inventive RNA preservation media is that it is bactericidal, but does not lyse cells. Therefore, the titer of pathogenic organisms will not change during storage of samples and skew apparent numbers, and samples can also be analyzed microscopically for additional information.

EXAMPLE 18

Use of RNA Preservation Media to Preserve Pathogens

Thousands of specimens each year are stored and shipped on dry ice to central laboratories that perform RNA analysis to detect pathogens. In an anticipated use, RNAlater™ or other inventive RNA preservation media may be used as a shipping buffer, preserving RNA in infectious, disease causing organisms. RNAlater™ or other inventive RNA preservation media will permit samples to be shipped at ambient or near-ambient temperatures without fear of RNA degradation. An organization that would benefit both by the extra degree of protection RNAlater™ or other inventive RNA preservation media would afford, plus realize a significant savings in shipping costs is The Centers For Disease Control (CDC), who receive many human and animal samples for pathogenic testing.

EXAMPLE 19

Use of RNA Preservation Media in FACS Sorting

Fluorescent Activated Cell Sorting (FACS) is a method with which cells in suspension can be separated based on differences in cell surface markers. We anticipate the use of RNAlater™ or other inventive RNA preservation media as a suspension solution for cells to be run through a FACS machine. In this way, the RNA in the cells would be preserved. Once the cells are sorted, intact RNA can be isolated for analysis.

EXAMPLE 20

Use of RNA Preservation Media to Preserve Soil Bacteria

With the advent of RT-PCR methodology to identify bacterial species, there is a growing need for methods to isolate soil bacteria away from soil for subsequent RNA isolation. However, RNA in bacteria is extremely labile and is rapidly degraded during the isolation protocol. An anticipated use of RNAlater™ or other inventive RNA preservation media is as a first step in RNA isolation from soil bacteria. Soil can be dispersed in RNAlater™ or other inventive RNA preservation media, instantly protecting the RNA within bacteria, but keeping the bacteria intact. The soil can then be safely removed by low speed centrifugation, then the bacteria can be recovered by centrifugation at higher speed. The RNAlater™ or other inventive RNA preservation media will prevent the RNA from being degraded during the isolation procedure.

EXAMPLE 21

Methods of Isolating RNA Preserved in RNAlater™ or other Inventive RNA Preservation Media Several methods of isolating RNA from tissue samples have been evaluated for suitability with RNA preservation media-preserved tissues. Several such methods can be practiced with kits available from Ambion. Of course, Ambion kits are not required for the isolation of RNA from RNA preservation media-preserved tissues, and the use of other methodologies or kits to isolate RNA from RNA preservation media-preserved tissues and cell is covered by this specification. For example, any known methods of isolating RNA, such as those of Boom et al. (selective binding and retention of nucleic acid to glass matrix—Qiaprep™, Qiagen, Inc.), Chomczynski et al. (Trizol™, MRC), Macfarlane et al. (Catrimox 14™, Iowa Biotechnology, Inc.), Bugos et al. (Guanidine:Lithium Chloride), or Auffray et al. (LiCl:urea extraction), or kits for the practice of such methods may be used in this regard.

The following specific examples describe the use of Ambion kits to isolate RNA from tissue samples or cells stored in RNAlater™ or other inventive RNA preservation media. It is contemplated that Ambion may choose to sell a combined kit for the preservation of RNA in tissue samples or cells, followed by the subsequent isolation of RNA from those samples.

EXAMPLE 22

Isolation of Cellular RNA from Samples Preserved in RNAlater™ or other Inventive RNA Preservation Media Using the Ambion ToTally RNA™ Kit The Ambion ToTally™ RNA kit is a Guanidinium/Acid Phenol method of preparing cellular RNA.

Figure 9:
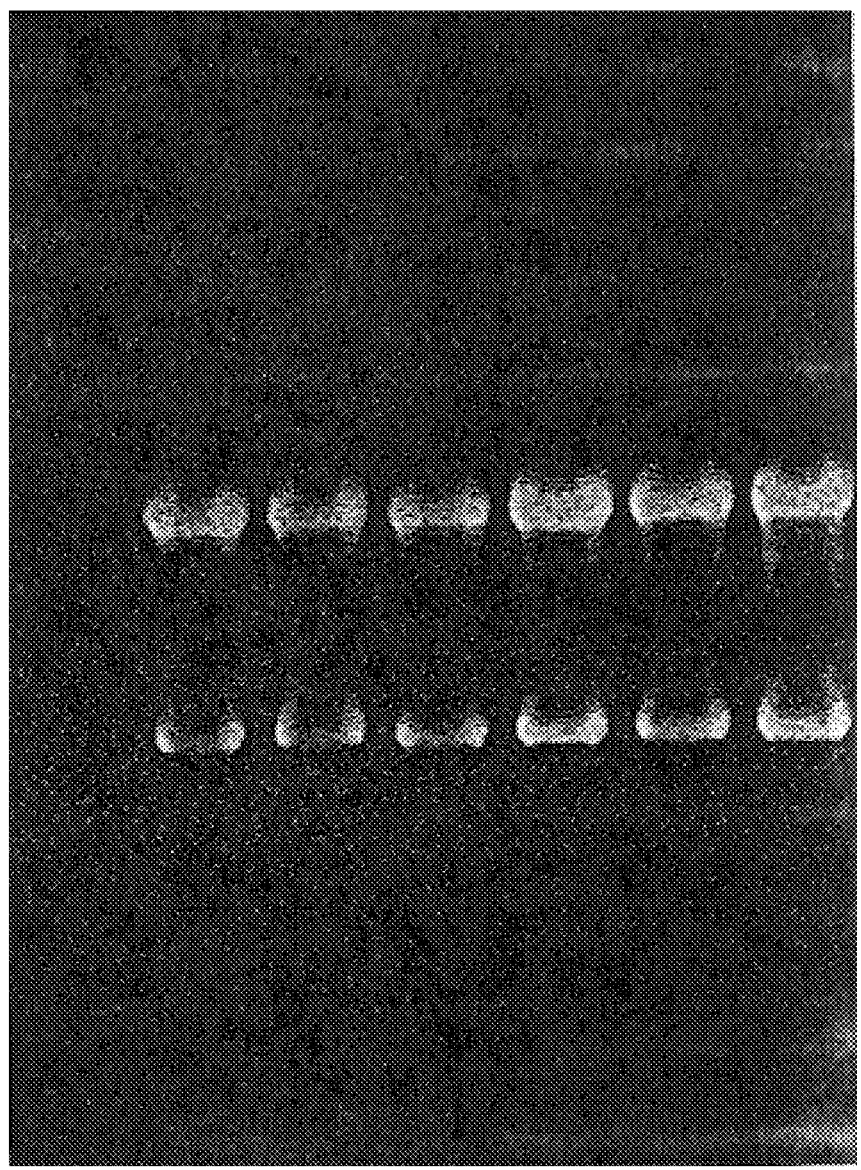

In order to demonstrate the utility of combining RNAlater™ or other inventive RNA preservation media preservation of tissue sample with the ToTally RNA™ procedure, tissue samples were removed from storage in RNAlater™ and homogenized in 10 volumes of a Guanidinium Isothiocyanate lysis solution consisting of 4M guanidinium hydrochloride, 0.5% sarcosine, 25 mM Sodium Citrate, 0.1M 2-mercaptoethanol. Proteins are removed by an extraction with an equal volume of phenol: chloroform (1:1), followed by a centrifugation to separate the aqueous and organic phases. The aqueous phase is recovered and extracted a second time with phenol at pH 4.7. This second extraction partitions any remaining proteins in the organic phase and the low pH forces any DNA into the organic phase. The RNA remains in the aqueous phase. The aqueous phase is recovered by centrifugation. The RNA is recovered from the aqueous phase by precipitation with 0.3M Sodium Acetate and 2.5 volumes of ethanol. Results are shown in FIG. 9.

EXAMPLE 23

Isolation of Cellular RNA from Samples Preserved in RNAlater™ or other Inventive RNA Preservation Media Using the Ambion RNAgueous™ Kit.

The Ambion RNAqueous™ kit is a Guanidinium lysis method for isolating RNA that does not require organic solvents. Instead, it relies upon the selective adsorption of RNA upon a glass fiber filter.

In order to demonstrate the utility of combining RNAqueous™ with RNAlater™ or other inventive RNA preservation media tissue samples were removed from storage in RNAlater™, transferred directly to the Guanidinium Isothiocyanate lysis solution provided in RNAqueous™ and homogenized. The homogenate was applied to a glass fiber filter and washed with several buffers, which remove protein and DNA. Pure RNA was then eluted from the filter with water. The coupling of RNAlater™ or other inventive RNA preservation media and RNAqueous™ has the advantage that no caustic or carcinogenic organic reagents (phenol, chloroform, ethanol, acetic acid, etc) are used throughout the procedure. Fresh samples or samples preserved in RNAlater™ were homogenized in 10 volumes of a solution consisting of 4M guanidinium hydrochloride, 1% sarcosine, 25 mM Sodium Citrate, 0.1M 2-mercaptoethanol, 2% Triton X-100. The homogenate is diluted 2x and passed over a glass fiber filter. Under these conditions, nucleic acids bind to the filter and proteins are washed away. Several sequential washes in high salt and ethanol differentially wash away the DNA, leaving only RNA bound to the filter. The RNA is subsequently recovered by elution with hot water. Results are shown in FIG. 9.

EXAMPLE 24

Use of Solid RNAlater to Preserve Nucleic Acid in Liquid Samples

The solid components of the preferred RNA preservation composition may be dissolved directly in a liquid sample to be stabilized, added to a sample/liquid mixture, added to a sample that has been placed in a liquid or present in a collection vessel prior to collection of a sample or sample/liquid mixture.

The solid components can be blended in a dry mixer to the proper composition such that when added to an aqueous sample and dissolved, the preferred salt, buffer, and chelator concentration is achieved in solution. The pre-measured aliquots of powdered, dry components can be loaded into sample collection vessels, and an appropriate volume of sample would be added. The collection vessel would then be agitated, dissolving the RNAlater components in the solution. This would minimize operator exposure to the sample, and would be a preferred method for stabilizing nucleic acids in a biological specimen such as blood or urine. Alternatively, the dry components can be pressed into tablet form and stored in bulk. Tablets would be a convenient format for storage and can be added in the correct quantity to a sample of any size in any type of container. This would be a preferred method for field collection of liquid samples from such sources as water reservoirs or sewage plants or the dairy industry. The primary advantages of using the RNA preservation reagent in dry mode would be weight savings in storage and transport, spills of solid components would be less likely, and volume savings in that preserving liquid samples with dry reagents would minimize the final volume of the sample.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 5,922,591
U.S. Pat. No. 5,921,396
U.S. Pat. No. 5,726,012
U.S. Pat. No. 5,090,420
Allewell, N. M., Sama, A., "The effect of ammonium sulfate on the activity of ribonuclease A." Biochemica et Biophysica Acta 341:484–488 (1974).
Auffray, C., Rougeon, F., "Purification of mouse immunoglobulin heavy chain messenger RNAs from total myeloma tumor RNA." Eur. J. Biochemistry Jun;107(2) 303–314 (1980).

Boom, W. R., Adriaanse, H., Kievits, T., Lens, P. F., U.S. Pat. No. 5,234,809 entitled: Process for Isolating Nucleic Acid.

Bugos R. C., Chiang, V. L., Zhang, X. H., Campbell, E. R., Podila G. K., Campbell W. H., "RNA isolation from plant tissues recalcitrant to extraction by guanidine." Biotechniques Nov;19(5)734–7 (1995).

Cairns, M. T., Church, S., Johnston, P. G., Phenix, K. V., Marley, J. J., "Paraffin-embedded tissues as a source of RNA for gene expression analysis in oral malignancy." Oral Diseases Sep;3(3):157–161 (1997).

Chomczynski, P., U.S. Pat. No. 5,346,994 entitled: Shelf Stable Product and Process for Isolating RNA, DNA, and Proteins.

Dimulescu et al., "Characterization of RNA in Cytologic Samples Preserved in a Methanol-Based Collection Solution," Molecular Diagnosis 3(2):67–72 (1998).

Esser, et al., "Isolation of full-sized mRNA from ethanol-fixed cells after cellular immunofluorescence staining and fluorescence-activated cell sorting." (FACS). Cytometry 1995 Dec 1;21(4):382–386.

Foss, R. D., Guha-Thakurta, N., Conran, R. M., Gutman, P., "Effects of fixative and fixation time on the extraction and polymerase chain reaction amplification of RNA from paraffin-embedded tissue." Comparison of two housekeeping mRNA controls. Diagn Mol Pathol Sep;3(3):148–155 (1994).

Houze, T. A., Gustavsson, B., "Sonification as a means of enhancing the detection of gene expression levels from formalin-fixed, paraffin-embedded biopsies." Biotechniques Dec;21(6):1074–1078 (1996).

Hurley et al., U.S. Pat. No. 5,256,571 entitled Cell Preservation Solution (1993)

Koopmans, M., Monroe S. S., Coffield, L. M., and Zaki, S. R., "Optimization of extraction and PCR amplification of RNA extracts from paraffin-embedded tissue in different fixatives." J.Virol Methods Jul; 43(2):189–204 (1993).

Lin L.-N., Brandts, J. F., "Refolding of ribonuclease in the presence and absence of ammonium sulfate pulses." Comparison between experiments and simulations. Biochemistry 26:1826–1830 (1987)

Macfarlane, D. E., U.S. Pat. No. 5,010,183 entitled: Process for Purifying DNA and RNA using Cationic Detergents.

Stanta G., Schneider, C., "RNA extracted from paraffin-embedded human tissues is amendable to analysis by PCR amplification." Biotechniques Sep;11(3):304 (1991).

What is claimed is:

1. A method of preserving RNA comprising:
   (i) obtaining a sample comprising at least one intact cell;
   (ii) providing a salt comprising at least one salt; and
   (iii) admixing the sample and the salt in a liquid to form an RNA preservation composition that infiltrates the cell and protects RNA in the cell from nucleases, wherein the final salt concentration in solution is between 10 g/100 ml and a saturating concentration.

2. The method of claim 1, wherein the sample is comprised in the liquid prior to admixing the sample with the salt.

3. The method of claim 1, wherein the sample comprises at least one blood cell and the liquid is blood serum.

4. The method of claim 1, wherein the liquid is water.

5. The method of claim 1, wherein the liquid is a buffer.

6. The method of claim 1, wherein the salt is in a solid form prior to admixing with the sample and the liquid.

7. The method of claim 1, wherein the salt is comprised in the liquid prior to admixing the sample with the salt.

8. The method of claim 1, wherein the salt is a sulfate salt.

9. The method of claim 8, wherein the salt is ammonium sulfate.

10. The method of claim 1, wherein the salt is present in solution at a final concentration of between 20 g/100 mL and the saturating concentration of the salt.

11. The method of claim 10, wherein the salt is present in solution at a final concentration of between 30 g/100 mL and 80 g/100 mL.

12. The method of claim 1, wherein the RNA preservation composition comprises at least two salts.

13. The method of claim 12, wherein the total salt concentration is present in solution at a final concentration of between 20 g/100 mL and 100 g/100 mL.

14. The method of claim 1, wherein the RNA preservation composition comprises a chelator of divalent cations.

15. The method of claim 1, wherein said RNA preservation composition comprises a buffer.

16. The method of claim 15, wherein said buffer has a pH between 4 and 8.

17. The method of claim 1, further comprising the step of isolating the preserved RNA.

18. The method of claim 17, wherein the RNA is isolated at a temperature that is greater than −20° C.

19. The method of claim 17, wherein the sample is stored prior to the isolation of the RNA.

20. The method of claim 19, wherein the sample is stored at temperatures greater than 0° C.

21. The method of claim 1, wherein the salt is provided in a collection vessel.

22. The method of claim 1, wherein the sample and the salt are admixed in a collection vessel.

23. The method of claim 1, wherein the salt is provided in a specimen collection container.

24. The method of claim 1, wherein the sample and the salt are admixed in a specimen collection container.

25. The method of claim 1, wherein the sample is a suspension of cells.

26. The method of claim 1, wherein the sample is a solid tissue sample.

27. The method of claim 1, wherein the sample is an entire organism.

28. The method of claim 27, wherein the organism is a pathogen.

* * * * *